United States Patent

Cohen et al.

[11] Patent Number: 6,132,380
[45] Date of Patent: Oct. 17, 2000

[54] METHOD AND APPARATUS FOR MEASURING PERFUSION OF BIOLOGICAL TISSUE BY BLOOD

[75] Inventors: Richard J. Cohen, Chestnut Hill; Derin A. Sherman, Lincoln; Robert H. Rubin, Brookline, all of Mass.

[73] Assignee: Massachusetts Institute of Technology, Cambridge, Mass.

[21] Appl. No.: 09/154,621

[22] Filed: Sep. 16, 1998

[51] Int. Cl.[7] .............. A61B 5/02; A61B 8/00; A61B 6/00; A61B 5/00

[52] U.S. Cl. .............. 600/481; 600/479; 600/437; 600/438; 600/300

[58] Field of Search .................. 600/481, 504, 600/479, 480, 437, 476, 438, 443, 445, 448, 449, 450, 454, 507, 300

[56] References Cited

U.S. PATENT DOCUMENTS

| | | | |
|---|---|---|---|
| 4,109,647 | 8/1978 | Stern et al. | 600/479 |
| 4,590,948 | 5/1986 | Nilsson | 600/479 |
| 4,867,165 | 9/1989 | Noller et al. | 600/479 |
| 5,233,994 | 8/1993 | Shmulewitz | 600/454 |
| 5,339,817 | 8/1994 | Nilsson | 600/479 |
| 5,361,769 | 11/1994 | Nilsson | 600/479 |
| 5,588,437 | 12/1996 | Byrne et al. | 600/479 |
| 5,766,127 | 6/1998 | Pologe et al. | 600/476 |
| 5,862,805 | 1/1999 | Nitzan | 600/479 |

OTHER PUBLICATIONS

Dymling et al, "Measurement of Blood Perfusion in Tissue Using Doppler Ultrasound", Ultrasound in Medicine and Biology, 1991, vol. 17, No. 5, pp. 433–444, 1991.

Buhrer et al. "Subtraction Procedure for the Registration of Tissue Perfusion with Doppler Ultrasound", *Ultrasound in Med. & Biol.* 22(5):651–658 (1996).

*Primary Examiner*—Cary O'Connor
*Assistant Examiner*—Navin Natnithithadha
*Attorney, Agent, or Firm*—Choate, Hall & Stewart

[57] ABSTRACT

Perfusion measurement method. The method includes detecting a signal emanating from the tissue and processing the signal to detect fluctuations substantially spatially correlated on a length scale less than 1 centimeter. The fluctuations are then analyzed to obtain a measure of perfusion. In one embodiment, the detected fluctuations are substantially correlated with fluctuations of a biological parameter such as the cardiac cycle or the respiratory cycle.

35 Claims, 4 Drawing Sheets

FIG.7a
LEG WITHOUT TOURNIQUET

| SKIN + FAT | MUSCLE |

FIG.7b
LEG WITH TOURNIQUET

| SKIN + FAT | MUSCLE |

METHOD AND APPARATUS FOR MEASURING PERFUSION OF BIOLOGICAL TISSUE BY BLOOD

BACKGROUND OF THE INVENTION

One of the most important problems in medicine and biology is measuring the flow of blood to organs. Adequate blood flow is essential to the health of organs as the flow of blood carries required nutrients to the organs and waste products away from the organs. Perfusion refers to the passage of blood through a vascular bed, usually capillaries, although the definition can also include both arterioles and venules. The flow of blood proceeds first through a branching network of arteries which spread out from the heart in much the same manner as the branches of a tree spread out from the trunk. At the end of the arterial network, the blood flows through capillaries which connect the network of arteries to the network of veins. The majority of nutrient/waste transfer occurs in the capillaries. Blockage anywhere in the vascular system will impede blood flow. When blood flow in a major artery or vein is diminished, so too is the flow of blood to all capillaries connected to that vessel. If the flow of blood ceases for a long period of time, then the quiescent blood will clot, thus eliminating the obstructed vessels as viable pathways for further blood flow.

Fall in tissue perfusion below a critical level results in tissue injury, cell death, and impaired organ function. This is a dynamic process termed ischemia-reperfusion injury which has several elements: impaired perfusion for a critical period of time, such that both leukocytes and vascular endothelium are activated, followed by further tissue injury when perfusion is reestablished. From this brief description, it is apparent that time is of the utmost importance in terms of limiting tissue injury, and precise measurements of tissue perfusion are essential for managing the condition. A wide variety of diseases are associated with impaired tissue perfusion and, when present to a major degree, the risk of full-blown ischemia-reperfusion injury of such vital organs as the heart, brain, kidneys, and gut. Conditions associated with impaired tissue perfusion include sepsis, hepatic cirrhosis, heart failure, shock of diverse etiologies, the post-operative state after major surgery, and critical illnesses of a variety of kinds. Powerful drugs are available to modify tissue perfusion, if reliable measurement technologies were available to assess the status of perfusion and the effects of an intervention. Such a strategy would help greatly in preventing or limiting the extent of renal failure, myocardial infarction, stroke, and other consequences of hypoperfusion and ischemia-reperfusion injury.

Such an approach would also have a role in the management of solid tumors. Extensive studies over the past 15 years have shown that tumor angiogenesis is an important element of the growth and development of solid tumors. Anti-cancer strategies that involve anti-angiogenesis drugs that decrease tumor perfusion are now in advanced clinical testing. A technology for assessing perfusion of tumor mass as a guide to clinical management is greatly to be desired.

A. Perfusion and Blood Flow

The capillaries are very small—slightly smaller than the size of a red blood cell—so the flow of blood through capillaries requires a finite positive pressure be maintained. The flow of blood through a small tube (vessel) is given by Darcy's law:

$$\dot{Q} = \frac{P_1 - P_2}{R} \quad (1.1)$$

where $\dot{Q}$ is the flow of blood, $P_1$ and $P_2$ refer to the hydrostatic pressure at the two ends of the tube, and R is the resistance to the flow of blood given by Poiseuille:

$$R = \frac{8\eta L}{\pi r^4} \quad (1.2)$$

where $\eta$ is the viscosity of blood, L is the length of the blood vessel, and r is the interior radius of the blood vessel.

There is stress in the vascular walls due to the pressure inside the blood vessels. The tension T in the vascular walls is given by Laplace:

$$T = \Delta P r \quad (1.3)$$

where $\Delta P$ refers to the difference in pressure between the inside and outside of the blood vessel. Since the capillary radius is very small (about 5 $\mu$m) compared to a typical arterial radius (about a few millimeters), the tension in the capillary wall is greatly reduced by a factor of roughly 10,000. However, the stress S in the arterial wall, $$S = T/w \quad (1.4)$$

is not much less than that in a major artery since the thickness of the capillary wall w is smaller by a factor of roughly 1000. Berne and Levy [Robert M. Berne and Matthew N. Levy, "Cardiovascular Physiology" 5th Edition, C.V. Mosby Company, St. Louis (1985)] report that stress in the aorta is about 6 times greater than stress in capillaries.

When stress is applied to elastic tissue, it deforms in proportion to the stress. The implications of this fact are that the capillaries are likely to expand as the pressure inside of them increases. Indeed, this is part (albeit a small part) of the reason why a finite positive pressure is required to maintain the flow of blood within the capillaries: they need to expand sufficiently before the blood cells can flow through them. In addition, finite pressure is required to deform the cells so that they can squeeze through the capillaries.

Lee and colleagues [Lee et al., "Evaluation of Pulsatile and Nonpulsatile Flow in Capillaries of Goat Skeletal Muscle Using Intravital Microscopy" Microvascular Research 48:316–327 (1994)] demonstrate that the blood flow in capillaries of goat muscle tissue is highly pulsatile and is strongly correlated in time with the cardiac cycle. Furthermore, they also show that the amplitude of the velocity fluctuations in the capillaries varies linearly with the pulse pressure.

There are also more subtle hydrodynamic effects which cause blood vessels to expand in response to a fluid impulse. Volobuev [A. N. Volobuev, "Fluid flow in tubes with elastic walls" Physics Uspekhi 38(2):169–178 (1995)] demonstrates soliton solutions to the hydrodynamic equations governing fluid flow in the vascular network. The soliton solutions are entirely non-linear in nature and are characterized by synchronous changes in intravascular pressure, cross-sectional area of the vessel, and blood flow velocity.

B. Imaging Blood Flow

Two basic methods have been used for measuring blood flow in tissue. The first involves the introduction of a contrast agent into the blood stream. The contrast agent is chosen to match a particular imaging modality so as to maximize the signal scattered from blood. For example, an X-ray contrast agent would strongly absorb X-rays, and an ultrasound contrast agent would strongly scatter ultrasound waves, and a radionuclide would emit radiation.

Contrast agents often do not measure the speed of blood flow. However, they still provide a direct measure of perfusion as they detect the quantity of accessible capillaries. This is because the flow rate through a given capillary is more or less the same as the flow through any other capillary provided that blood is flowing through the capillaries. Thus, contrast agents provide a "digital" measure of blood flow: they measure the number of capillaries which are "on" in the sense that they provide a conduit for blood flow.

The primary advantage of contrast agents is that they provide an unambiguous signal of high intensity which can be quantified with precision. Unfortunately, introduction of contrast agents can be highly invasive with possible clinical complications. For example, there is a 0.1% chance of killing a patient when performing an angiogram due to an adverse reaction to the contrast agent.

The second method for measuring blood flow involves detecting the Doppler shift from moving blood. [P. Peronneau and A. Herment, "Principles of Spectral Doppler" in "Cardiac Ultrasound" Churchill Livingstone, 1993] The Doppler shift arises when a wave phenomenon interacts with a moving object. In the case of blood, the moving objects are blood cells. Examples of Doppler shift detection include both laser light scattering and Doppler ultrasound detection. One big advantage of Doppler shift detection is that it is completely non-invasive and thus avoids the medical complications inherent to contrast agents. Another advantage is that the Doppler shift detects the motion of blood, rather than the mere presence of blood. This permits quantification of blood flow directly. [P. A. J. Bascom and R. S. C. Cobbold, "Origin of the Doppler Ultrasound Spectrum from Blood" IEEE Transactions on Biomedical Engineering 43(6) :562–571 (1996)] [Donald A. Christopher et al., "A High-Frequency Pulsed-Wave Doppler Ultrasound System for the Detection and Imaging of Blood Flow in the Microcirculation" Ultrasound in Medicine & Biology 23(7):997–1015 (1997)] Unfortunately, the Doppler shift arises not only from motion in blood but also motion in tissue. In the case of ultrasound, this limits the quantifiable velocity range to motion greater than approximately one centimeter per second.

C. Signals and Waves

When a wave travels through a medium in which the speed of the wave is equal to a constant c, then the relationship between the frequency $f$ and the wavelength $\lambda$ is given by $$c = f\lambda \tag{1.5}$$

It is sometimes convenient to discuss signals in terms of the frequency $f$ and at other times $\lambda$. We reserve the right to use either of these descriptions where appropriate.

When processing signals, there will often be several different frequencies involved. The transmitter carrier refers to the frequency of the signal produced by the transmitter. The signal frequency refers to the signal received after the transmitted signal has been scattered from an object. The Doppler shift is the difference between the carrier and signal frequency arising from motion of the scattering object. The detection carrier refers to a signal processing method which compares the incoming signal to a reference signal of definite frequency. The digitization frequency refers to the rate at which data is collected and quantized. Often, large sections of tissue are repeatedly sampled. The rate at which a given portion of tissue is re-sampled is known as the sampling frequency.

When a source (transmitter) of definite frequency $f_0$ moves with respect to a receiver, a Doppler shift is observed. When the speed of the transmitter v is much less than the speed of the signal c then the Doppler shift $f_D$ is given by the equation $$f_D = f_0 \frac{v}{c} \cos\theta \tag{1.6}$$

where $\theta$ is the angle between the velocity vector of the moving object and the line which passes through both the transmitter and receiver. In many situations, the source of the signal (transmitter) is the same as the receiver in which case the system is known as a transceiver. When a moving object is probed with a transceiver, there are effectively two Doppler shifts: one shift occurs between the transmitter and the moving object and the second shift occurs between the moving object and the receiver. In this case, the measured Doppler shift is twice that of equation (1.6).

[Stephan O. Dymling et al., "Measurement of Blood Perfusion in Tissue Using Doppler Ultrasound" Ultrasound in Medicine & Biology 17(5):433–444 (1991)]

[Roger Eriksson et al., "Evaluation of Doppler Ultrasound for Blood Perfusion Measurements" Ultrasound in Medicine & Biology 17(5):445–452 (1991)]

[Roger Eriksson et al., "Blood Perfusion Measurements with Multifrequency Doppler Ultrasound" Ultrasound in Medicine & Biology 21(1):49–57 (1995)]

D. Lock-in Amplifier

In many situations, a physical system will respond to an applied stimulus with a very weak response which is often hard to detect due to the ambient level of noise. One method for detecting the weak response is to modulate the applied stimulus at a known frequency and then demodulate the measured signal at that known frequency. This method is the basis of a device known as a Lock-in Amplifier and has the property that it can reliably detect small signals in the presence of considerable noise.

E. Quadrature Amplitude Demodulation

Figure 2:
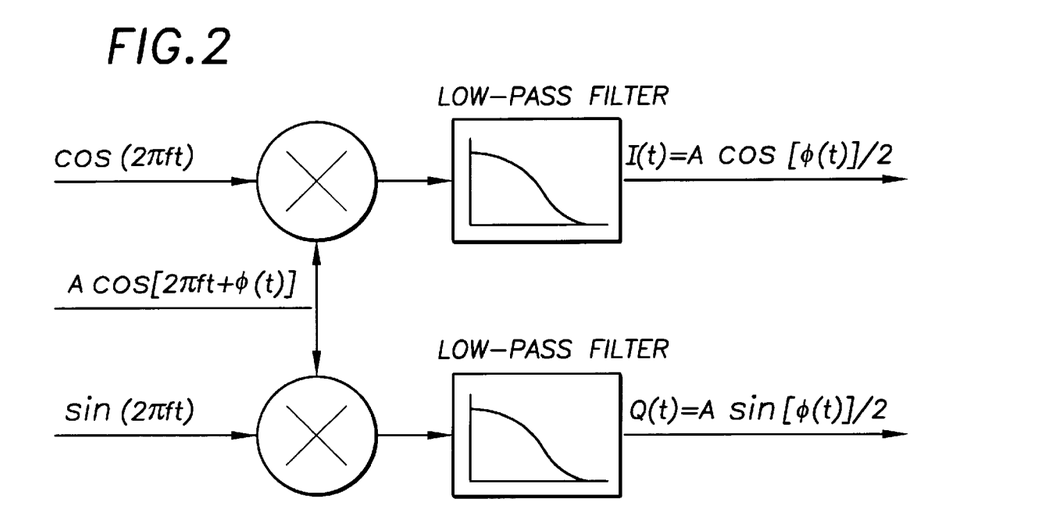
FIG. 2 is a block diagram illustrating operation of quadrature amplitude demodulation (QAM).

The Doppler shift is often detected using the method of Quadrature Amplitude Demodulation (QAM). The QAM detector takes the original signal and generates two new signals known as I and Q. The I signal is generated by first multiplying the original signal by $\cos(2\pi ft)$ where $f$ is the carrier frequency, and then low-pass filtering. The Q signal is computed in a similar fashion, except that a sine wave is used instead of a cosine. This process is illustrated in FIG. 2. [Helen F. Routh, "Doppler Ultrasound" IEEE Engineering in Medicine and Biology pp. 31–40 (November–December 1996)].

Figure 3:
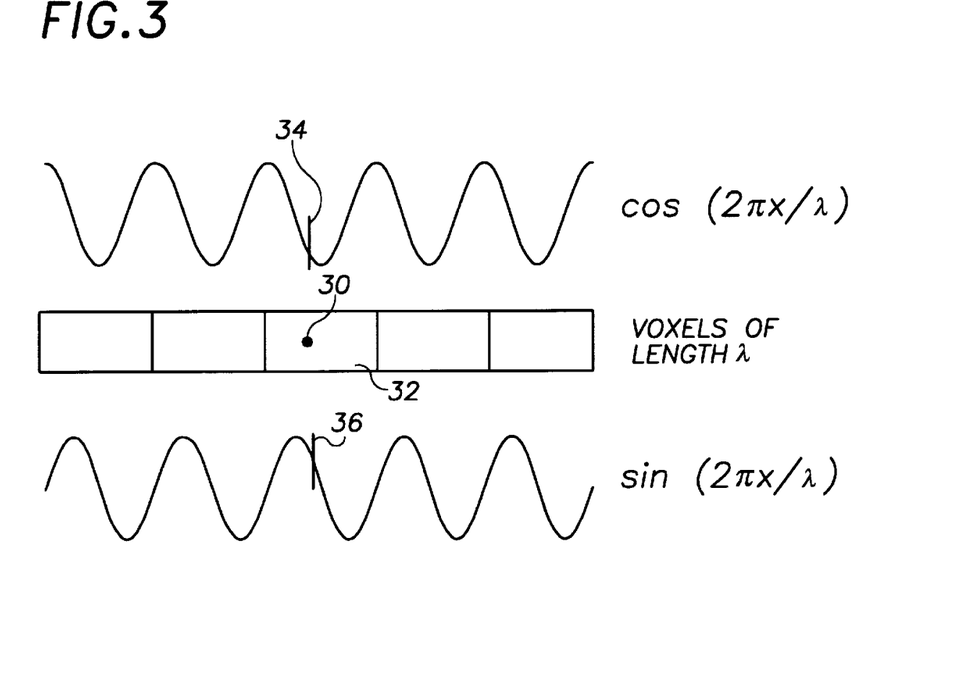
FIG. 3 is a graphical representation of the sine-cosine (SC) mean position and the carrier sine and cosine waves.

The QAM detection process can be illustrated by examining a signal, A $\cos(2\pi ft)$, emanating from a single point located a distance $\lambda(n+\phi(t)/2\pi)$ from the detector, as shown in FIG. 3. The I component of the QAM signal is given by the formula $$I(t) = \langle A\cos(2\pi ft - 2n\pi - \phi(t)) \times \cos(2\pi ft) \rangle \tag{1.7}$$

where the angle-brackets represent a time-average over one cycle. The value of I is therefore given by $$I(t) = A < [\cos(2\pi ft)\cos(\phi(t)) - \sin(2\pi ft)\sin(\phi(t))] \times \cos(2\pi ft) \quad (1.8)$$

$$= A < [\cos^2(2\pi ft)\cos(\phi(t)) - \cos(2\pi ft)\sin(2\pi ft)\sin(\phi(t))] > \quad (1.9)$$

$$= A\left[<\cos^2(2\pi ft)\cos(\phi(t))> - <\frac{1}{2}\sin(4\pi ft)\sin(\phi(t))>\right] \quad (1.10)$$

The ($4\pi ft$) term averages to zero over a full cycle, but the $\cos^2$ term averages to ½. Therefore, the I component yields the value $A\cos((\phi))/2$. In a similar fashion, the Q component yields the value $A\sin((\phi))/2$.

The utility of the QAM detection process is illustrated in the case where the particle moves uniformly toward (or away from) the detector. In this case, the phase $\phi$ is given by the equation $$\phi(t)=\phi_0+2\pi vt/\lambda \quad (1.11)$$

where v is the speed of the particle and $\phi_0$ is the value of $\phi$ at the time t=C. In this case, $$I(t)=A\cos(\phi_0+2\pi vt/\lambda)/2 \quad (1.12)$$

$$Q(t)=A\sin(\phi_0+2\pi vt/\lambda)/2 \quad (1.13)$$

where the value $v/\lambda$ is the Doppler shift. In practice, a transceiver is used to probe the Doppler shift, and so the value measured is $2v/\lambda$.

For the QAM detection method to work properly, it is required that the transmitter carrier frequency and the QAM carrier frequency be identical. The only requirement on the digitization frequency is that it must be at least twice the Doppler shift frequency.

F. Windowed Cross Correlation

One of the problems associated with Doppler shift detection is known as aliasing. Aliasing is caused when the magnitude of the QAM phase shift is greater than $\pi$. Since it is impossible to distinguish between a phase shift of $+\pi$ and $-\pi$, motion which causes a phase shift greater than $\pi$ will be aliased back down to a motion with phase shift less than $\pi$. One technique which can circumvent this problem is the Windowed Cross Correlation (WCC). [O. Bonnefous and P. Pesque, "Time Domain Formulation of Pulse-Doppler Ultrasound and Blood Velocity Estimation by Cross Correlation" Ultrasonic Imaging 8:73–85 (1986)] The WCC technique sends out two pulses at times $t_1$ and $t_2$ and then varies the time-delay between the two signals so as to maximize the cross correlation. More formally, if the two signals, $s_1$ and $s_2$ received at times $t_1$ and $t_2$, respectively are given by the equations $$s_1(t)=r(t)+n_1(t) \quad (1.14)$$

$$s_2(t)=r(t+d)+n_2(t) \quad (1.15)$$

where r(t) is the signal due to backscatter from the tissue and $n_1$ and $n_2$ are random noise signals, then the tissue motion can be estimated by maximizing the cross-correlation function $$R(t)=\int s_1(t)s_2^*(t+\tau)dt \quad (1.16)$$

with respect to the time shift $\tau$. In other words, $R(\tau)$ is maximized when $\tau=d$.

In practice, only short segments of each signal are compared using the windowed cross-correlation function $$R_W(t_0, \tau) = \int_{t_0}^{t_0-T_0} s_1(t)s_2^*(t+\tau)dt \quad (1.17)$$

where $t_0$ indicates the position of the tissue segment being investigated and $T_0$ indicates the size of the window where tissue is compared. The value of $\tau$ which maximizes the WCC gives the tissue displacement at the position $ct_0/2$ which occurred between time $t_1$ and $t_2$, thus the velocity is $$v(ct_0/2)=d/(t_2-t_1) \quad (1.18)$$

There are several advantages to the WCC technique. It avoids the problem of aliasing because it estimates a time-delay rather than a phase shift. It also performs considerably better than the standard Doppler technique because emitted pulses are often broadband while the Doppler technique is based on a narrowband model. [I. A. Hein and William D. O'Brien, Jr., "Current Time-Domain Methods for Assessing Tissue Motion by Analysis from Reflected Ultrasound Echoes-A Review" IEEE Transactions on Ultrasonics, Ferroelectrics and Frequency Control 40(2):84–102 (1993)] Also, since the WCC pulse can be very narrow, it is possible to simultaneously improve both the range estimate as well as the velocity estimate; in the Doppler technique, an improvement in range estimate comes with a decrease in the precision of the velocity estimate. [Chihiro Kasai et al., "Real-Time Two-Dimensional Blood Flow Imaging Using an Autocorrelation Technique" IEEE Transactions on Sonics and Ultrasonics SU-32(3) (1985)].

One of the large drawbacks of the WCC is that its performance depends greatly upon the window size $T_0$. In addition, when the velocity profile is non-uniform or non-stationary, then the WCC performs poorly. Xu et al. [Xiao-Liang Xu, Ahmed H. Tewfix, James F. Greenleaf, "Time Delay Estimation Using Wavelet Transform for Pulsed-Wave Ultrasound" Annals of Biomedical Engineering 23(5):612–621 (1995)] use a wavelet technique to circumvent the problems associated with a fixed window size. They simulate ultrasound beams and find that they are able to make significantly better measurements than the standard WCC. Unfortunately, their velocity resolution (a few centimeters per second) falls far short of that required to measure perfusion (about 0.1 mm/s).

G. Tissue Motion Compensation

Perfusion of tissue by blood is hard to detect noninvasively for several reasons. First, the motion of tissue is of comparable magnitude to the motion of the blood flow in capillaries. Thus, the motion of the tissue often masks the motion of the blood. Second, while the motion of tissue is spatially coherent over large length scales, the motion of blood in capillaries is spatially coherent over very short length scales. Thus, even though the mean velocity of blood through a single capillary may be large, the mean flow averaged over several capillaries will be close to zero. Third, for many imaging modalities, e.g., ultrasound, the signal from blood is much weaker than that from the surrounding tissue. These difficulties can be partially surmounted by processing techniques which remove that component of the signal due to the bulk motion of tissue. We shall refer to these techniques as tissue motion compensation.

Bührer et al. in "Subtraction Procedure for the Registration of Tissue Perfusion with Doppler Ultrasound," Ultrasound in Medicine & Biology, 22(5):651–658 (1996) have devised a subtraction procedure which compares the Doppler signal from a pair of spatially separated ultrasound beams. Their method operates under the assumption that the phase shift common to both beams will be due to the bulk motion of tissue, while the phase difference between the two beams will be indicative of perfusion. This makes a great deal of sense, since the phase shift shared by the two beams is spatially correlated over a few millimeters, while the phase difference is due to motion which is uncorrelated over the same few millimeters. They find that their method is able to partially remove many (but not all) tissue motion artifacts. Unfortunately, their method uses a Fourier transform method and is unable to spatially localize the motion. Thus, they can measure the effects of perfusion, but are unable to form an image.

Brands et al. in "A Radio Frequency Domain Complex Cross-Correlation Model to Estimate Blood Flow Velocity and Tissue Motion by Means of Ultrasound," Ultrasound in Medicine & Biology 23(b):911–920 (1997) seek to improve the WCC by processing the signal in the complex domain. They find that the complex cross-correlation function is determined by the equation $$R(k, i) = (S + N_i) \cdot \exp\left\{ \frac{-\pi \overline{f}_{nc}^2 (k - \phi \cdot i)^2}{Q^2} + j \cdot 2\pi \cdot \overline{f}_{nc} (k - \phi \cdot i) \right\} \quad (1.19)$$

where R(k,i) is the complex cross-correlation function, k denotes the tissue depth (voxel), i denotes sample time, S denotes signal power, $N_i$ denotes noise power at time i, Q is the quality factor (spatial mean frequency divided by bandwidth), $\phi$ is the phase shift, j is the square-root of −1, and $\overline{f}$ and $\overline{f}_{nc}^2$ represent the spatial mean frequency and the spatial mean frequency square, respectively. They find that their complex cross correlation method can reliably assess tissue motion with high resolution due to its unbiased velocity estimation. However, while their method can be used to map both tissue motion and blood flow, it does not appear to have the resolution to image blood flow in capillaries.

H. Other Methods for Measuring Velocities and Tissue Characteristics

Rather than trying to measure perfusion directly, there are a number of methods which measure velocity distributions within tissue as a means to characterize the tissue. Derumeaux and colleagues [Genevieve Derumeaux et al., "Doppler Tissue Imaging Quantitates Regional Wall Motion During Myocardial Ischemia and Reperfusion" Circulation 97:1970–1977 (1998)] show that it is possible to use the Doppler signal scattered from tissue to identify ischemia in the myocardium. Their method works by detecting the change in the pattern of cardiac contraction when the heart muscle (myocardium) is deprived of blood. While their method permits a non-invasive assessment of perfusion, it does not actually image the regions of the myocardium which are (or are not) being perfused.

Alam and Parker [Sheik Kaisar Alam and Kevin J. Parker, "The Butterfly Search Technique for Estimation of Blood Velocity" Ultrasound in Medicine and Biology 21(5):657–670 (1995)] have developed a hybrid technique which tracks blood flow using a method which combines some features of the Doppler technique along with some features of the cross-correlation technique. While their method performs quite well in the presence of noise, the error in the measured velocity is typically on the order of a couple of centimeters per second. Therefore, this method lacks sufficient resolution to detect blood flow in the microvasculature.

Another method for measuring blood flow is based on measuring temporal fluctuations of ultrasound speckle patterns. These patterns arise from constructive and destructive interference of coherent ultrasound signals scattering off tissue. Yeung, Levinson and Parker [Fai Yeung et al., "Multilevel and Motion Model-Based Ultrasonic Speckle Tracking Algorithms" Ultrasound in Medicine & Biology 24(3):427–441 (1998)] have developed a method which uses speckle patterns to identify motion within tissue. Their method is able to both identify and characterize different types of tissue movement such as translation, rotation, compression, and shear. Their intended application of this method is ultrasonic elastography, which images the elastic characteristics of tissue using ultrasound. In many cases, changes in tissue elasticity are accompanied by changes in perfusion. [Arno Schmidt-Trucksass et al., "Assessment of Carotid Wall Motion and Stiffness with Tissue Doppler Imaging" Ultrasound in Medicine & Biology 24(5):639–646 (1998)] Unfortunately, this method lacks sufficient resolution to resolve the flow of blood due to perfusion.

A great deal of work has been done in studying the problem of perfusion. Most methods depend upon contrast agents, and many of these methods do not permit accurate measurements of perfusion. The few methods that do not depend upon contrast agents do not permit accurate measurements of perfusion. Yet, despite all these attempts, there is still no satisfactory method for noninvasively measuring perfusion at the microvascular level.

SUMMARY OF THE INVENTION

Measuring perfusion of biological tissue by blood is a medically important problem which can not be satisfactorily solved using conventional techniques. Our solution to this problem is based on the observation that blood flow in the microvasculature is pulsatile: microvessels have a pulse in much the same manner as larger arteries. The pulse is temporally correlated with blood pressure fluctuations, such as the heart beat. However, the spatial distribution of microvessels is spatially correlated only over short length scales. Thus, we measure perfusion by quantifying fluctuations in tissue which are temporally correlated with blood pressure fluctuations (heart beat) but are spatially uncorrelated over length scales greater than a centimeter. Our method quantifies perfusion by measuring the strength of these fluctuations. In the preferred embodiment, our invention utilizes an ultrasound technique which is completely noninvasive, inexpensive, and requires minimal training to master and maintain the equipment. Therefore, this technique should be readily available to any hospital which requires it.

In one aspect, the method of the invention for measuring perfusion of biological tissue by blood includes detecting a signal emanating from the tissue. The signal is processed to detect fluctuations substantially spatially correlated only on a length scale less than one centimeter. The fluctuations are then analyzed to obtain a measure of perfusion. In one embodiment, the method further includes the step of detecting fluctuations which are substantially correlated with fluctuations of a biological parameter such as blood pressure or blood flow. The biological parameter may be correlated with, for example, the cardiac cycle, the respiratory cycle or an externally induced blood flow. It is preferred that energy be coupled into the biological tissue, the energy causing the emanation of the signal from the tissue. A preferred form of energy is ultrasound energy and the length scale of fluctuation is less than one millimeter. Other energy modalities include magnetic energy and the signal is a nuclear magnetic resonance image of the tissue; light energy in which the signal is light scattered from the tissue; electrical energy in which the signal is an electrical impedance image; and an electric potential generated by the Hall effect.

The signal may be characterized by both mean position of scatterers within each voxel and the total quantity of scatterers within each voxel. An arithmetic mean position may be calculated via a dual linear ramp method. In another aspect, the mean position is calculated by a SC mean position method. The method may also include calculating the temporal Fourier coefficient of the fluctuation signal and the signal may be integrated over an integral number of known blood pressure fluctuation cycles.

The method of this invention includes a generalization of the concept of a lock-in amplifier. Since the total signal is often much greater than the component of the signal due to blood perfusion, the blood pressure is modulated and fluctuations in the signal which correlate with the blood pressure are integrated so as to remove noise and other effects not related to perfusion. The source of blood pressure modulation can be due to the natural beating of the heart (cardiac cycle), natural or paced breathing (respiratory cycle) or externally induced, e.g., by an inflatable cuff.

A second concept involves the relative scattering strength of blood and tissue. In the case of ultrasound, blood scatters less than 1% the signal scattered by tissue. Therefore, rather than trying to examine the flow of blood directly, we examine the spatial fluctuations in tissue directly and treat blood as though it were invisible. The spatial fluctuations in tissue arising from the changes in the size (and position) of the microvessels caused by fluctuating blood pressure are used to quantify perfusion. In other imaging modalities, e.g., the Hall effect, the blood may be more prominent than the tissue, so the tissue is treated as transparent and only the motion of blood is considered.

A third concept involves the manner in which the signal is processed. We show that it is possible to measure the mean tissue position within a given voxel using a method which uses the same processing electronics as quadrature amplitude demodulation although configured in a somewhat different fashion. Fluctuations in these mean positions provide a more sensitive measure of tissue (and blood) motion than fluctuations in the signal intensity. The signal is processed to produce both mean amplitude and mean position measurements. The mean amplitude measurements provide coarse-scale information which can be processed using conventional techniques, e.g., windowed cross correlation. The mean position measurements provide the fine-scale position information which permits the perfusion signal to be detected.

A fourth concept utilizes the idea that signal fluctuations which are correlated over length scales greater than one millimeter are related to the bulk motion of tissue. Fluctuations which are not correlated between adjacent pixels are related to perfusion. This method thus permits the bulk motion of tissue to be filtered from the signal so that only the perfusion signal remains. We show that our method of tissue motion compensation functions as well or better than other tissue motion compensation methods which have been considered.

DESCRIPTION OF THE PREFERRED EMBODIMENT

Figure 1:
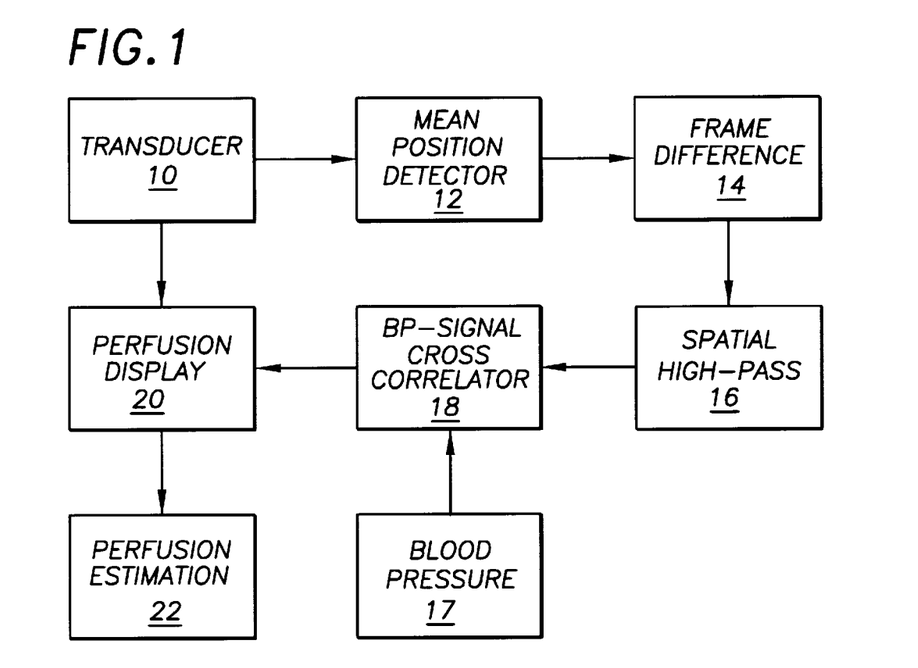
FIG. 1 is a block diagram of a preferred embodiment of the apparatus of the invention.

In the preferred embodiment, illustrated in the block diagram of FIG. 1, an ultrasound pulse generated by an ultrasound transducer 10 is transmitted into tissue (not shown) and the signal scattered off the tissue (referred to as the "signal") is passed to a mean position detector 12 which generates a frame of data containing both the mean amplitude and mean position. The mean position is calculated for each voxel of tissue. The voxel is defined by the cross-sectional area of the ultrasound beam multiplied by the speed of sound in tissue and divided by the digitizing frequency of the analog to digital converter. Entire video frames, each one corresponding to a slice of tissue (which could be a one-dimensional beam, a two-dimensional slice, or a three-dimensional section), are captured in sequence. The same region of tissue is scanned several times, and the differences between consecutive frames are calculated in a frame difference module 14 generating a frame containing the motion information between two frames. These frame differences are actually images of tissue motion. Then, the motion due to coherent (or bulk) tissue motion is removed by performing a spatial high-pass filter 16. The resulting data now contain only noise and the perfusion signal. The perfusion signal is extracted from the noise by cross-correlating with the known blood pressure 17 variations in a cross-correlator 18. This result can then be used to either directly display or compute the perfusion within a region of tissue, or combined with the original signal to form a standard "color flow" image displayed in a display 20. In addition, a region of the perfusion image may be selected and perfusion estimation can be calculated by integrating the perfusion signal over the selected region in a perfusion estimation module 22.

The color flow image is a combination of signal intensity and the perfusion measurement combined together so that both elements are easily discernable. A standard method for generating a color flow image is to use the intensity of the ultrasound signal to generate the brightness (luminance) component of a video signal, and to use the perfusion signal as the color (chrominance) component of the same video signal.

Figure 7A:
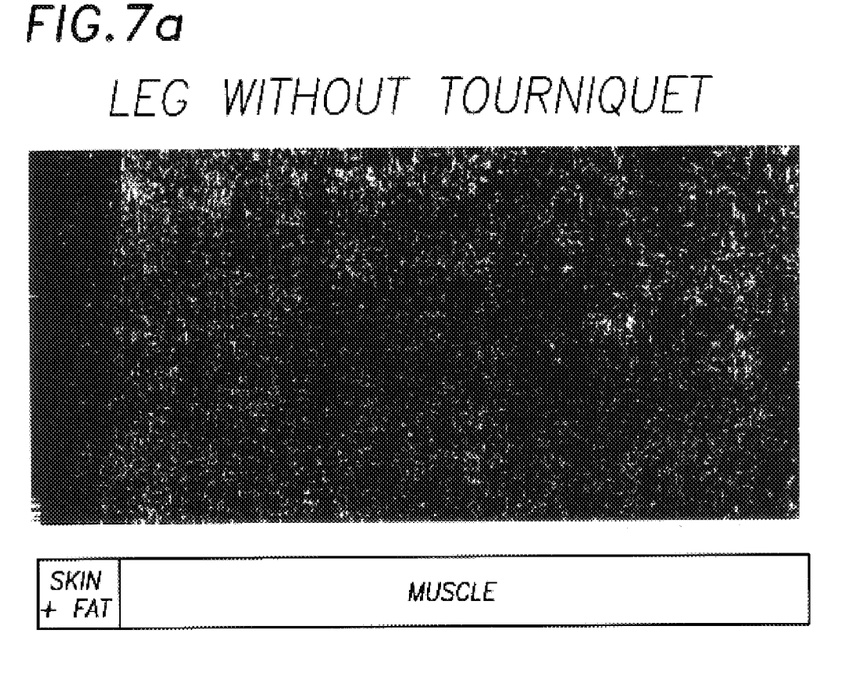
FIGS. 7a and 7b are perfusion images of a cross-section of leg.
Figure 7B:
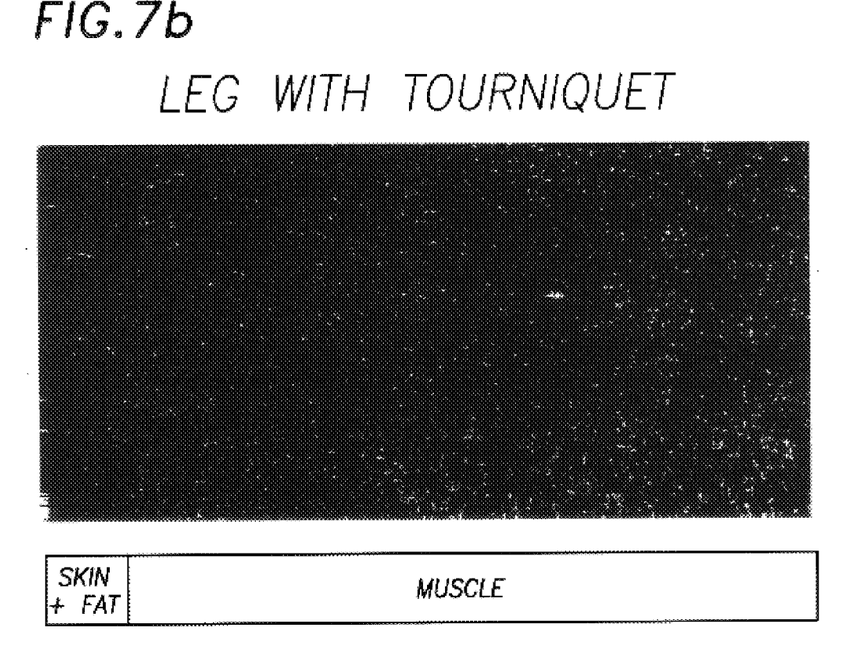

A typical display of the perfusion signal alone is shown in FIGS. 7a and 7b which show an image of a cross-section of a human leg magnified by about a factor of three. In the FIG. 7a muscle is clearly shown to be perfused while the skin and fat have very little blood flow. FIG. 7b shows the same leg, but this time a tourniquet (not shown) has been applied which drastically reduces the flow of blood. The decrease in the perfusion signal is clearly evident. Due to experimental limitations, the perfusion signal in FIGS. 7a and 7b was calculated without the aid of the blood-pressure cross-correlation procedure. Had the cross-correlation been included in the calculation, we anticipate a significant reduction in the noise present in the signal. Note that the small bright streaks along the left edge of FIGS. 7a and 7b are electronic artifacts unrelated to either the perfusion algorithm or the original ultrasound signal.

Using the mean tissue position is advantageous because it can detect very small tissue displacements and it does not bias in favor of tissue which contains a large number of high-strength scatterers. In addition, it is a simple matter to perform tissue motion-compensation using the mean tissue position as the signal parameter. Note that the tissue may move over a length greater than a voxel thickness. In this event, a "coarse-position" measurement is performed using a standard windowed cross-correlation (WCC) technique to determine local tissue movement. The WCC will only measure tissue displacement with an accuracy equal to the thickness of a voxel. However, once the bulk tissue motion is known, it is then possible to use the mean position measurements to quantify the sub-voxel tissue motion. In an ideal embodiment, the sampling frequency would be high enough to preclude the need for the WCC.

A. Pressure Variation as a Means of Probing Perfusion

Rather than trying to directly quantify the steady-state component of the blood flow, we seek to probe perfusion by generalizing the concept of a lock-in amplifier to include signal changes which are correlated with arbitrary blood pressure fluctuations. Since the total signal is often much greater than the component of the signal due to blood perfusion, the blood pressure is modulated and fluctuations in the signal which correlate with the blood pressure are integrated so as to remove effects not related to perfusion. The source of blood pressure modulation can be due to the natural beating of the heart (cardiac cycle), natural or paced breathing (respiratory cycle) or externally induced, e.g., by an inflatable cuff.

The general idea is that the signal due to perfusion will be greater when the pressure is greater, and smaller when the pressure is smaller. Since the pressure fluctuations are known, it is possible to cross-correlate the signal with the pressure fluctuations with a possible time delay. This will drastically reduce the noise from the signal and enhance that component of the signal due to perfusion.

In a preferred embodiment, the blood pressure cross-correlation (module 18) can be performed by using a QAM technique using the relevant blood pressure frequency (e.g., cardiac cycle, respiratory cycle, etc.) as the QAM carrier frequency. In this preferred embodiment, the input signal is from the spatial high-pass filter 16, and the sine and cosine QAM inputs are generated in reference to the known blood pressure cycle from the blood pressure detector 17. By integrating the QAM signal, only that Fourier component of the signal which matches the blood pressure variation is extracted from the velocity measurements.

B. Measuring the Mean Position

The word "mean" has many different meanings. In the context of this invention, the "mean position" is any physical quantity which has the following properties:

1. A distribution of scatterers, $f(x)$, possesses reflection symmetry about a point $x_0$ if $f(x_0-x)=f(x_0+x)$. If the distribution is symmetric about $x_0$, then the mean is equal to $x_0$. In the special case where the distribution consists of a single scatterer at $x_0$, then the mean is also equal to $x_0$.

2. If an entire distribution of scatterers is shifted by an amount $\Delta x$, then the mean position also shifts by an amount $\Delta x$.

3. The convolution of two distributions, $f$ and $g$ is written as $f*g$. If the distribution $f$ has a mean $\bar{x}_f$ and the distribution $g$ has a mean $\bar{x}_g$ then the convolution $f*g$ has a mean equal to $\bar{x}_{f*g}=\bar{x}_f+\bar{x}_g$.

In one preferred embodiment, the mean position is the simple arithmetic mean calculated by dividing the first moment of the distribution by the zeroth moment of the distribution. In another preferred embodiment, the mean position is calculated using the following formula $$\bar{x}_{SC} = \frac{\lambda}{2\pi}\phi \qquad (4.1)$$

$$\phi = \tan^{-1}\left(\frac{S}{C}\right) \qquad (4.2)$$

Figure 5:
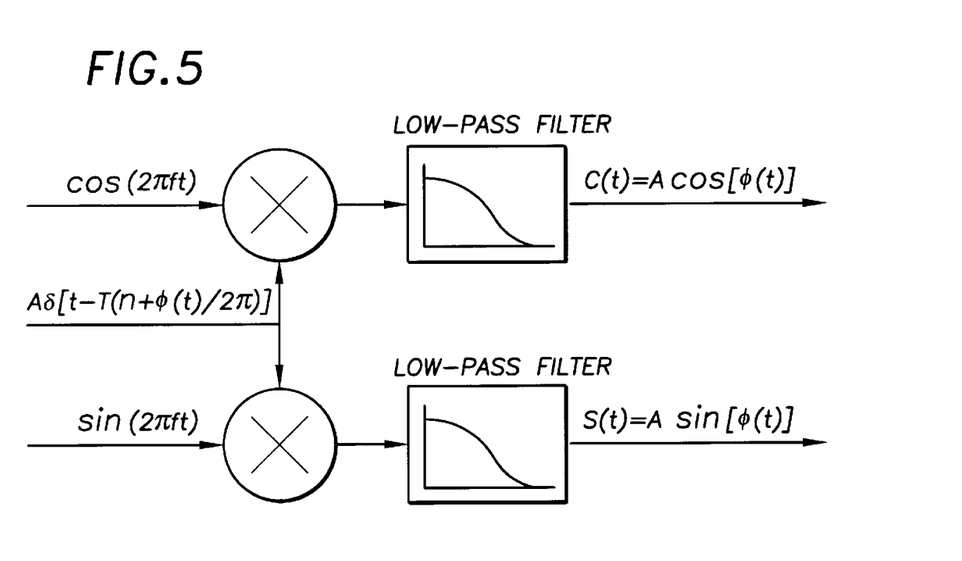
FIG. 5 is a block diagram illustrating the operation of the SC mean position algorithm.

The S signal is generated by first multiplying the original signal by $\sin(2\pi ft)$ where $f$ is the carrier frequency (typically the digitization frequency), and then averaging over one digitization cycle. The C signal is computed in a similar fashion, except that a cosine wave is used instead of a sine. This process is illustrated in FIG. 5. This technique uses electronics which are essentially identical to those used in the QAM technique shown in FIG. 2.

Classically, QAM is performed when the input signal is of the form of a sine wave: the frequency of the signal and the QAM carrier frequency are identical. FIG. 2 illustrates this idea showing that the signal from a single scatterer located at a distance $\lambda(n-\phi/2\pi)$ from the receiver (within voxel n) will generate a QAM signal with Q/I=tan $\phi$ when the scattered signal is a conventional sine wave. However, it should be noted that our SC method of measuring the mean position is not limited to signals which are of the form of sine waves. Indeed, there is no relationship between the signal being analyzed and the SC carrier frequency. Rather, the SC components serve to analyze the signal in terms of a pair of orthogonal functions. It is convenient if the digitizing frequency and the SC carrier frequency are identical, but this condition is not necessary. All that is required is that the SC frequency be lower than the digitizing frequency and that the phase relationship between the SC carrier and the voxels be maintained.

FIG. 5 illustrates how our SC mean position is determined from a signal which is a sharp spike ($\delta$-function) scattered from a single particle located at a distance $\lambda(n+\phi/2\pi)$ from the receiver, as shown in FIG. 3. In this Figure, a single scatterer 30 is shown within a single voxel 32. Vertical lines 34 and 36 intersect the sine waves at the point at which the carrier waves are sampled. In the case of a single scatterer, the arc tangent of the ratio of these values gives the position of the scatterer. In the case of several scatterers the arc tangent gives the mean position of the scatterers. We will now show that this SC mean position satisfies the criteria for a mean position.

Figure 6:
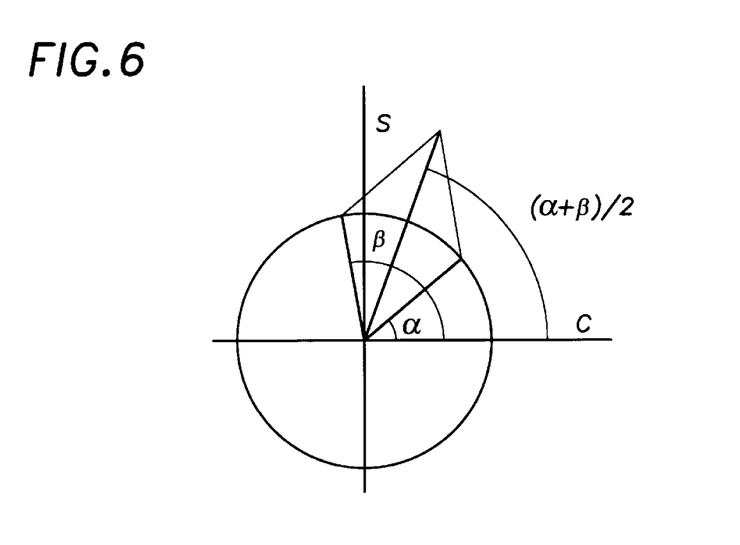
FIG. 6 is a graphical illustration of a trigonometric identity which demonstrates that the SC mean is identical to the arithmetic mean in the case where two identical scatterers are present in a single voxel.

We can show that the SC method of measuring position satisfies the first property of the mean using the following trigonometric identity. If there are two scatterers located at positions $\lambda\alpha$ and $\lambda\beta$ then the mean position is located at $$\tan^{-1}\left(\frac{\sin(\alpha) + \sin(\beta)}{\cos(\alpha) + \cos(\beta)}\right) = \frac{\alpha + \beta}{2} \qquad (4.3)$$

which is equivalent to demonstrating the first property of the mean. This trigonometric identity is illustrated in FIG. 6. The S and C components of each signal are plotted as a two-dimensional vector where the S and C components are equal to the magnitude of the scattering amplitude multiplied by the sine and cosine, respectively, of the position of the scatterer represented as a phase. The vector sum of two vectors of equal magnitude bisects the angle between the two vectors, thus proving the trig identity. In a similar fashion, any distribution which possesses reflection symmetry about an angle $\bar{\phi}$ will also have a SC mean of $\bar{\phi}$.

The second property of the mean can be demonstrated via a simple change in the coordinate system. In essence, the mathematical statement is that if $$\frac{A_1 \sin(\phi_1) + A_2 \sin(\phi_2) + A_3 \sin(\phi_3) + \cdots}{A_1 \cos(\phi_1) + A_2 \cos(\phi_2) + A_3 \cos(\phi_3) + \cdots} = \tan(\bar{\phi}) \qquad (4.4)$$

then $$\frac{A_1 \sin(\phi_1 + \Delta\phi) + A_2 \sin(\phi_2 + \Delta\phi) + A_3 \sin(\phi_3 + \Delta\phi) + \cdots}{A_1 \cos(\phi_1 + \Delta\phi) + A_2 \cos(\phi_2 + \Delta\phi) + A_3 \cos(\phi_3 + \Delta\phi) + \cdots} = \tan(\bar{\phi} + \Delta\phi) \qquad (4.5)$$

This is also easily demonstrated using a S-C vector diagram. Rotating each vector through an angle $\Delta\phi$ and then taking the vector sum is equivalent to rotating the entire sum of vectors through an angle $\Delta\phi$. This essentially amounts to the statement that vector addition commutes with rotations.

The third property of the mean can be proven using the Convolution theorem. If the Fourier transforms of $f$ and $g$, are written as $\hat{f}$ and $\hat{g}$, respectively, then the Fourier transform of the convolution is equal to the product $$\widehat{f * g} = \hat{f} \cdot \hat{g} \qquad (4.6)$$

In the Fourier domain, the SC method of measuring mean position of a distribution $f$ is equivalent to extracting the phase of the complex number defined by $\hat{f}$ evaluated at the SC carrier frequency.

Since the phase of the complex product is equal to the sum of the phases of the two complex numbers, the third property of the mean holds for the SC method for measuring mean position.

The SC components of the signal can also be used to compute the mean amplitude of the signal within each voxel. The mean amplitude is equal to the magnitude of the S-C vector, given by the amplitude $$A = \sqrt{S^2 + C^2}. \qquad (4.7)$$

Figure 4:
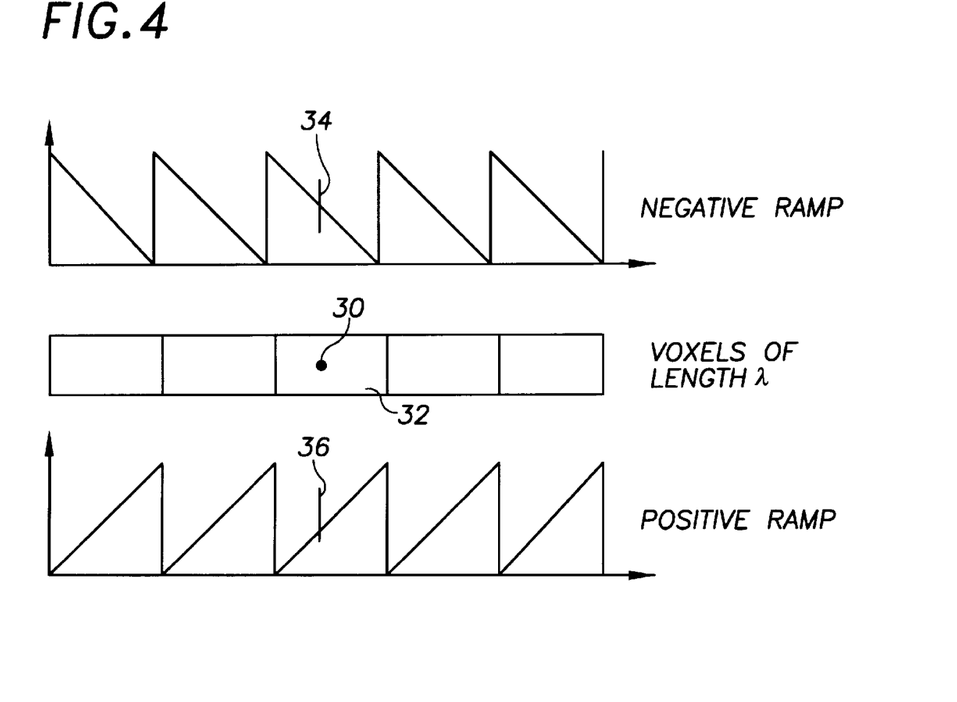
FIG. 4 is graph illustrating the relationship between the dual linear ramp mean position and the positive and negative ramps.

Another preferred method for computing the mean position is the Dual Linear Ramp method which relies on a technique which is very similar to the SC mean position, except that the carrier signals consist of a pair of triangle waves rather than a pair of sine waves. This is illustrated in FIG. 4. If we denote the signal generated by modulating the signal with the negative slope ramp as $I_-$ and the signal generated by modulating the signal with the positive slope ramp as $I_+$, then the "phase" $\phi'$ is given by the equation $$\phi' = \frac{2\pi}{\frac{I_-}{I_+} + 1} \qquad (4.8)$$

where the signals $I_-$ and $I_+$ are given by the equations $$I_-(n) = \int_{x=n\lambda}^{x=(n+1)\lambda} \left[1 - \frac{x - n\lambda}{\lambda}\right] s(x) dx \qquad (4.9)$$

$$I_+(n) = \int_{x=n\lambda}^{x=(n+1)\lambda} \frac{x - n\lambda}{\lambda} s(x) dx \qquad (4.10)$$

where n is the index of the voxel and $s(x)$ is the signal. Note that the value of $\phi$ determined by the dual linear ramp method is exactly equal to the arithmetic mean position of the scatterers within each voxel multiplied by $2\pi$. The proof is straightforward. Assume that there are a set of scatterers located throughout the voxel at positions $x_1, x_2, X_3, \ldots$ and that the scattering strength of each scatterer is denoted by $A_1, A_2, A_3, \ldots$, respectively. Then the values of the linear ramp QAM components are given by $$I_- = A_1(1-x_1) + A_2(1-x_2) + A_3(1-x_3) + \qquad (4.11)$$

$$I_+ = A_1 x_1 + A_2 x_2 + A_3 x_3 + \qquad (4.12)$$

and the mean position is given by $$\bar{x} = \frac{\lambda}{\frac{I_-}{I_+} + 1} \qquad (4.13)$$

$$= \frac{1}{\frac{\sum_k A_k(1 - x_k)}{\sum_k A_k x_k} + 1} \qquad (4.14)$$

$$= \frac{\sum_k A_k x_k}{\sum_k A_k} \qquad (4.15)$$

which, by definition, is the arithmetic mean position.

The mean amplitude of the signal within each voxel is easily calculated given the $I_+$ and $I_-$ components:

$$A = I_+ + I_- \qquad (4.16)$$

Although the SC mean position and the dual linear ramp mean position share many mathematical properties, they are not identical. One notable difference involves the concept of destructive interference. While the dual linear ramp mean samples all scatterers independent of their position, the SC mean ignores the presence of some scatterers. In particular, when two scatterers of equal strength A are placed a distance $(2n-1)\lambda/2$ apart, where n is an integer, then the signals from the two scatterers will cancel each other out. Consider a situation where these two scatterers are added to a distribution which has $S = S_0$ and $C = C_0$. If the first scatterer is at position $x_1$ then the second scatterer is at position $x_1 + (n+1)\lambda/2$, thus $$S = S_0 + A \sin(2\pi(x_1/\lambda)) + A \sin(2\pi(x_1/\lambda) + (2n+1)\pi) \qquad (4.17)$$

$$= S_0 + A \sin(2\pi(x_1/\lambda)) - A \sin(2\pi(x_1/\lambda)) \qquad (4.18)$$

$$= S_0 \qquad (4.19)$$

showing that the two scatterers do not contribute to the value of S. A similar argument shows that the two particles do not contribute to the value of C, thus demonstrating that the two scatterers do not contribute to the SC mean.

It is important to note that this interference effect is unrelated to interference effects due to the wave nature of the signal pulse, rather this is purely a phenomenon intrinsic to the calculation of the SC mean. One consequence of this effect is that the mean position is altered upon a dilation of the distribution. Consider a situation where the mean position is located at 0. If the distribution is uniformly dilated by a factor a i.e. moving each scatterer located at a position x to a position ax, then the dual linear ramp mean position remains at the origin 0. However, this is not the case for the SC mean. Consider the case where there are three scatterers of equal strength located at $$x_1 = -\frac{1}{12}\lambda, \; x_2 = 0, \text{ and } x_3 = \frac{5}{12}\lambda.$$

Due to destructive interference, the scatterers at $x_1$ and $x_3$ vanish and only the scatterer at $x_2$ appears in the SC mean calculation. However, if there is a dilation by a factor of 2, then the values of S and C are given by $$S = A\sin\left(2\pi\frac{-1}{6}\right) + A\sin(0) + A\sin\left(2\pi\frac{5}{6}\right) \quad (4.20)$$

$$= -\sqrt{3}\,A \quad (4.21)$$

$$C = A\cos\left(2\pi\frac{-1}{6}\right) + A\cos(0) + A\cos\left(2\pi\frac{5}{6}\right) \quad (4.22)$$

$$= 0 \quad (4.23)$$

which corresponds to a shift in the SC mean position by $\lambda/4$. The non-linear nature of the SC mean interference phenomenon can be exploited to increase the sensitivity to perfusion effects. For example, if the wavelength of the SC carrier is chosen such that it approximately matches the mean capillary separation length divided by a small integer power of 2, then any change in capillary size or position will be greatly enhanced by the interference effect.

C. Removing Bulk Tissue Motion

Bulk tissue motion is correlated at length scales greater than a critical length scale, which is approximately one millimeter. Velocity fluctuations smaller than this critical length scale are due to the effects of perfusion. Thus, to extract the perfusion signal, the velocity signal is spatially high-pass filtered. In a preferred embodiment, the spatial high-pass filter is performed by taking each voxel, averaging the velocities of the surrounding voxels, and subtracting this local mean velocity from the center voxel. This amounts to calculating that part of the tissue motion which is uncorrelated with the surrounding local tissue motion. In another preferred embodiment, the spatial high-pass filter is performed using a Daubechies 4-tap wavelet. While this is mathematically equivalent to the previous procedure, it is computationally more efficient.

D. Clinical Implications

Conventional methods for measuring perfusion usually rely on contrast agents or Doppler shift. The problem with contrast agents is that they are invasive. In the case of Doppler shift, it is difficult (or even impossible) to extract a measurement of perfusion as the signal scattered from blood can't be separated from the signal scattered from tissue. Our method is completely noninvasive, so permits measurements to be performed on patients in a variety of clinical settings. The patient could be monitored at bedside, during surgery, and even at the scene of an accident. In many cases, such as heart attack and stroke, it is essential to assess perfusion as the first step in prescribing an effective treatment, and this assessment must be done as quickly as possible. Since the equipment used to perform these measurements is inexpensive, easy to use, easy to maintain, and portable, this method has the potential to revolutionize many forms of medical treatment.

What is claimed is:

1. Method for measuring perfusion of biological tissue by blood comprising:
   detecting a signal emanating from the tissue;
   processing the signal to detect fluctuations substantially spatially correlated only on a length scale less than one centimeter; and
   analyzing the fluctuations to obtain a measure of perfusion.

2. The method of claim 1 further including the step of detecting fluctuations which are substantially correlated with fluctuations of a biological parameter.

3. The method of claim 2 wherein the biological parameter is correlated with the cardiac cycle.

4. The method of claim 2 wherein the biological parameter is correlated with the respiratory cycle.

5. The method of claim 2 wherein the biological parameter is correlated with an externally induced blood flow.

6. The method of claim 2 wherein the biological parameter is blood pressure.

7. The method of claim 2 wherein the biological parameter is blood flow.

8. The method of claim 1 or claim 2 comprising coupling energy into the biological tissue, the energy causing the emanation of the signal from the tissue.

9. The method of claim 1 wherein the length scale of the fluctuation is less than one millimeter.

10. The method of claim 8 wherein the energy is ultrasound energy.

11. The method of claim 10 wherein the signal emanating from the tissue is an ultrasound signal scattered from the biological tissue.

12. The method of claim 8 wherein the energy is magnetic and the signal is a nuclear magnetic resonance image of the tissue.

13. The method of claim 8 wherein the energy is light and the signal is light scattered from the tissue.

14. The method of claim 1 or claim 2 wherein the signal is a video microscopy image.

15. The method of claim 1 or claim 2 wherein the signal is an electrical impedance image.

16. The method of claim 1 or claim 2 wherein the signal is an electric potential generated by the Hall effect.

17. The method of claim 1 or claim 2 wherein the signal is characterized by both mean position of scatterers within each voxel and the total quantity of scatterers within each voxel.

18. The method of claim 17 wherein the arithmetic mean position is calculated via a dual linear ramp method.

19. The method of claim 17 wherein the mean position is calculated via a SC mean position method.

20. The method of claim 2 further including calculating the temporal Fourier coefficient of the fluctuating signal.

21. The method of claim 2 wherein the fluctuating signal is integrated over an integral number of known blood pressure fluctuation cycles.

22. The method of claim 1 or claim 2 wherein perfusion is measured in real time.

23. The method of claim 1 or claim 2 wherein the perfusion measurement is utilized diagnostically as a basis for therapeutic intervention.

24. The method of claim 23 wherein the intervention is surgical revascularization.

25. The method of claim 23 wherein the intervention is thrombolysis.

26. The method of claim 23 wherein the intervention is pressor therapy.

27. The method of claim 23 wherein the intervention is some form of anticoagulation or other type of pharmacologic intervention.

28. The method of claim 1 or claim 2 wherein serial measurements are used to monitor the response to therapeutic interventions.

29. The method of claim 28 wherein serial measurements are used in a clinical situation where tissue hypoperfusion is a significant concern, and where demonstration of such hypoperfusion might lead directly to effective corrective intervention.

30. The method of claim 29 wherein the clinical situation consists of patients undergoing general anesthesia.

31. The method of claim 29 wherein the clinical situation consists of patients undergoing surgery.

32. The method of claim 29 wherein the clinical situation consists of trauma.

33. The method of claim 29 wherein the clinical situation consists of patients in shock.

34. The method of claim 29 wherein the clinical situation consists of septic patients.

35. The method of claim 29 wherein the clinical situation consists of those individuals requiring care in an intensive care unit.

* * * * *